United States Patent [19]

McCombie et al.

[11] Patent Number: 4,882,429

[45] Date of Patent: Nov. 21, 1989

[54] STEREOSPECIFIC PREPARATION OF (3S,4R,5R)-3-(1-HYDROXYETHYL)-4-BENZOYLOXY-AZERIDINONES FROM L-(−)-THEONINE

[75] Inventors: Stuart W. McCombie, Caldwell; Michael P. Kirkup, Somerset, both of N.J.; Amy Sommese Boland, Pittsburgh, Pa.

[73] Assignee: Schering Corporation, Kenilworth, N.J.

[21] Appl. No.: 835,392

[22] Filed: Mar. 3, 1986

[51] Int. Cl.⁴ .................. C07D 205/08; C07B 41/12; C07B 37/10; A61K 301/24
[52] U.S. Cl. .................. 540/357; 540/200; 549/548; 560/250
[58] Field of Search .......................... 540/357

[56] References Cited

U.S. PATENT DOCUMENTS 4,614,614 9/1986 Ernest et al. ............... 540/200

FOREIGN PATENT DOCUMENTS 2144419 3/1985 United Kingdom .

OTHER PUBLICATIONS

Derwent 85-038254/07 (Be 900275-A published Feb. 1, 1985).
Hanessian, et al., J.A.C.S. 107, 1438-9 (Mar. 1985).
Yanagisawa, et al., Tetrahedron Letters 24, 1037-1040 (1983).
Shiozaki, et al., Tetrahedron 40, No. 10, 1795-1802 (1984).
Shiozaki, et al., Heterocycles, 22, 1725-6 (1984).
Shiozaki, Tet. Letters 22, 5205 (1981).

*Primary Examiner*—Mark L. Berch
*Attorney, Agent, or Firm*—Gerald S. Rosen; Thomas D. Hoffman

[57] ABSTRACT

Azetidinones represented by the formula

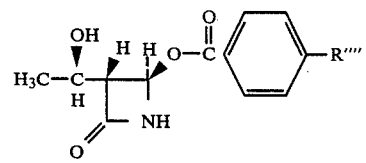

are prepared by a multistep process from L-(−)-theonine via an epoxyamide.

9 Claims, No Drawings

STEREOSPECIFIC PREPARATION OF (3S,4R,5R)-3-(1-HYDROXYETHYL)-4-BENZOYLOXY-AZERIDINONES FROM L-(−)-THEONINE

BACKGROUND

This invention relates to a stereospecific process for producing azetidinones which are useful as intermediates for preparing penems and carbapenems. More particularly, this invention relates to stereospecific processes for producing an azetidinone represented by the formula

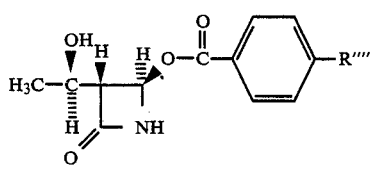

wherein R'''' is hydrogen, halogen or lower alkyl, from L-threonine by converting the L-threonine to an epoxyamide then to the azetidinone. The azetidinone is converted to penems and carbapenems by a series of steps, all of which are known in the art.

The process of this invention provides a means for production of azetidinones of specific stereochemistry which are intermediates for stereodefined penems and carbapenems by utilizing readily available, inexpensive starting materials.

Hanessian, et al., J.A.C.S. 107, 1438–9 (March 1985) discloses a process of making azetidinones from L-threonine via an epoxyamide. The process is similar but not identical to the invention described herein.

Yanagisawa, et al., Tetrahedron Letters 24, 1037 (1983) disclose a process for making phenylsulfonylazetidinones from L-threonine, via an epoxyamide.

Shiozaki, et al., Heterocycles, 22, 1725 (1984) disclose preparation of cyanoazetidinones from 2,3-epoxybutyric acid, an intermediate in the process of this invention.

Shiozaki, et al., Tetrahedron, 40, 1795 (1984) disclose a process of transforming L-threonine stereospecifically to an azetidinone used for making the carbapenem thienamycin.

BRIEF DESCRIPTION OF THE INVENTION

This invention provides means to prepare an azetidinone represented by the formula

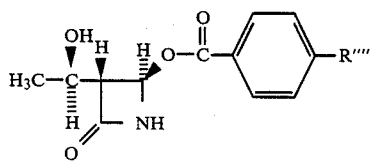

wherein R'''' is hydrogen, halogen or lower alkyl, from L-(−)-threonine in multistep processes via an epoxyamide represented by the formula

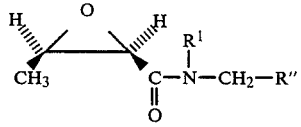

wherein R'' is

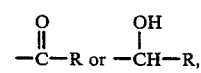

R is phenyl or phenyl substituted with halogen, preferably chlorine, or lower alkyl, preferably methyl;

R' is methoxyphenyl, preferably para methoxyphenyl, or dimethoxy phenyl, preferably 3,4 dimethoxy phenyl or allyl. Some of the compounds within the scope of formula II are novel compounds, i.e., those represented by the following formula

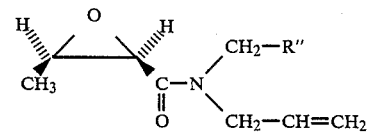

wherein R and R'' are as defined for formula II. Other novel intermediates are represented by the formula

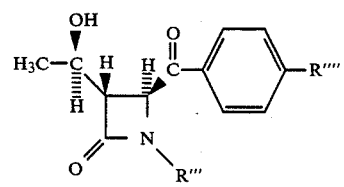

wherein R''' is H, allyl, vinyl methyl or formyl and R'''' is hydrogen, halogen or lower alkyl.

DETAILED DESCRIPTION

There are three routes to produce the compound of formula I, the first and most preferred route, designated Reaction Scheme A comprises the steps (a) reacting an aqueous acidic solution of L-(−)-threonine with sodium bromide and sodium nitrite to produce a compound represented by the formula

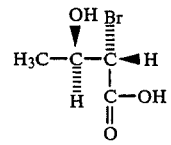

(b) reacting the compound produced in step (a) with an alkali metal base, to produce a compound represented by the formula

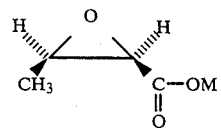

wherein M is an alkali metal.

(c) reacting the compound produced in step (b) with oxalyl chloride to produce the compound represented by the formula

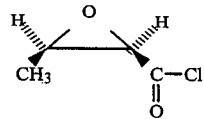

(d) reacting, without isolating, the compound produced in step (c) with a compound represented by the formula

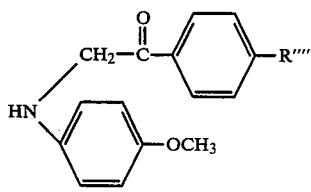

wherein R'''' is hydrogen, halogen or lower alkyl, in the presence of an organic base to produce a compound represented by the formula

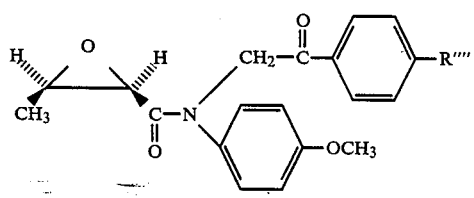

wherein R'''' is as defined for compound 7.

(e) reacting the compound produced in step (d) with lithium hexamethyldisilazide or potassium carbonate in DMF to produce a compound represented by the formula

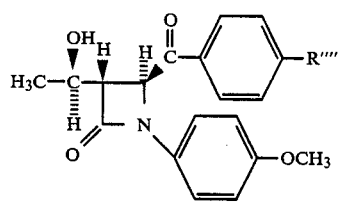

wherein R'''' is as defined for compound 7.

(f) reacting the compound produced in step (e) with aqueous ceric ammonium nitrite to produce a compound presented by the formula

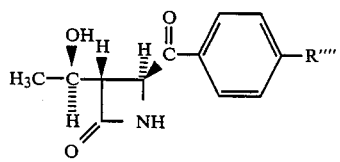

wherein R'''' is as defined for compound 7.

(g) reacting the compound produced in step (f) with m-chloroperoxybenzoic acid to produce a compound represented by the formula

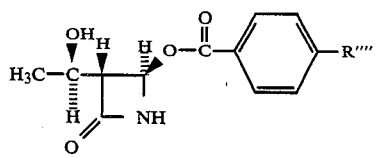

wherein R'''' is as defined for compound 7.

The second route designated Reaction Scheme B comprises the steps (a) reacting an aqueous acidic solution of L-(−)-threonine with sodium bromide and sodium nitrite to produce a compound represented by the formula

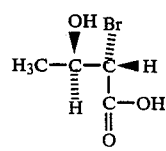

(b) reacting the compound produced in step (a) with acetyl chloride followed by oxalyl chloride or thionyl chloride to produce a compound represented by the formula

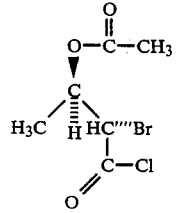

(c) reacting the compound produced in step (b) with a compound represented by the formula

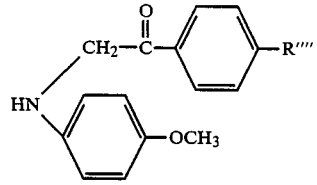

wherein R'''' is hydrogen, halogen or lower alkyl, in the presence of an organic base to produce a compound presented by the formula

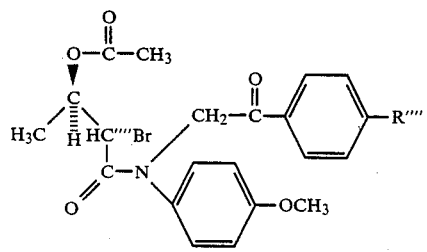

wherein R'''' is as defined for compound 7

(d) reacting the compound produced in step (c) with aqueous alcoholic potassium carbonate to produce a compound represented by the formula

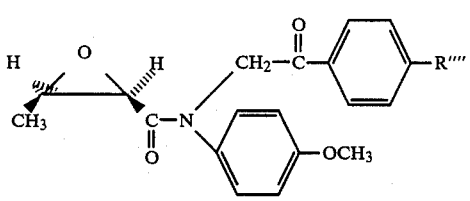   8 wherein R'''' is as defined for compound 7

(e) reacting the compound produced in step (d) with lithium hexamethyldisilazane to produce a compound represented by the formula

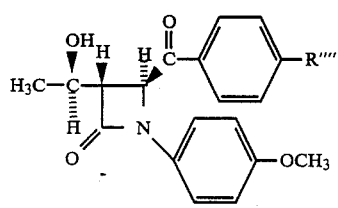   9 wherein R'''' is as defined for compound 7

(f) reacting the compound produced in step (e) with aqueous ceric ammonium nitrate or ozone to produce a compound presented by the formula

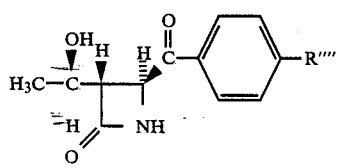   10 wherein R'''' is as defined for compound 7

(g) reacting the compound produced in step (f) with m-chloroperoxybenzoic acid to produce a compound represented by the formula

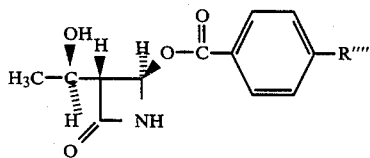   11 wherein R'''' is as defined for compound 7.

A third route designated Reaction Scheme C comprises the steps (a) reacting a compound represented by the formula

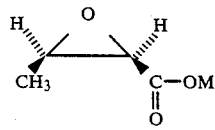   3 wherein m is an alkali metal with pivaloyl chloride to produce a compound represented by the formula

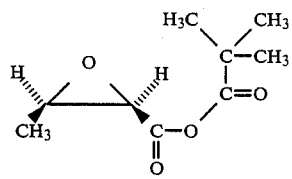   14

(b) reacting, in situ, the compound produced in step (a) with N-allyl-2-amino-1-phenylethanol in the presence of an organic base to produce a compound represented by the formula

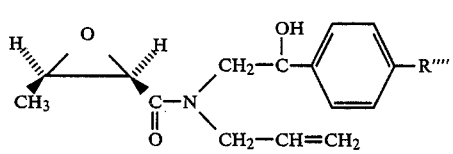   17 wherein R'''' is as defined for compound 7.

(c) reacting the compound produced in step (b) with chromic anhydride in dilute sulfuric acid to produce a compound represented by the formula

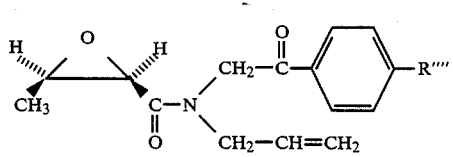   18 wherein R'''' is as defined for compound 7.

(d) reacting the compound produced in step (c) with lithium hexamethyldisilazide to obtain a compound represented by the formula

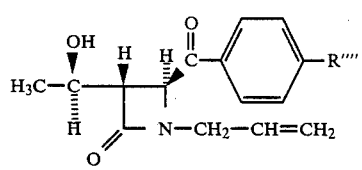   19 wherein R'''' is as defined for compound 7.

(e) reacting the compound produced in step (b) with a transition metal catalyst, preferably rhodium chloride, to obtain a compound represented by the formula

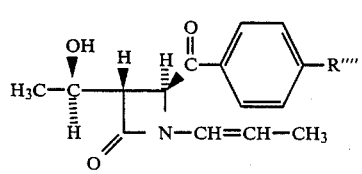   20 wherein R'''' is as defined for compound 7.

(f) reacting the compound produced in step (e) either with (1) ozone to obtain a compound represented by the formula

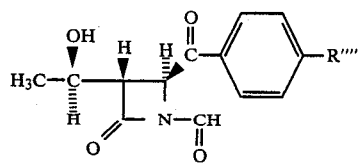

wherein R'''' is as defined for compound 7. or with (2) potassium permanganate to produce compound 10

(g) reacting the compound produced in step (f) (1) with an inorganic aqueous base to obtain a compound represented by the formula

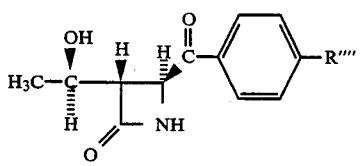

wherein R'''' is as defined for compound 7.

(h) reacting the compound produced in step (g) with m-chloroperoxybenzoic acid to produce a compound represented by the formula

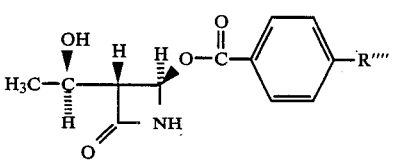

wherein R'''' is as defined for compound 7.

As used herein "lower alkyl" means straight or branched chain alkyl groups having from 1 to 7 carbon atoms, e.g. methyl, ethyl, propyl, isopropyl, butyl, t-butyl, pentyl, hexyl, neopentyl, dimethyl butyl and the like. Preferred is methyl.

"Halogen" means chlorine or bromine, with chlorine preferred.

"Alkali metal base" means sodium or potassium hydroxide with potassium hydroxide preferred.

"Inert organic solvent" means an organic solvent which is non-reactive under the reaction conditions, e.g. tetrahydrofuran (THF), lower alkanols, preferred is methanol or ethanol; methylene chloride, acetonitrile and the like.

"Inorganic base" means alkali metal carbonates or hydroxides with potassium carbonate preferred.

The process of the invention can be carried out by three Reaction Schemes. In one Reaction Scheme, designated Scheme A, L-(−)-threonine is converted to a compound of formula II via a β-methylglycidate, which is then converted to compound 10 which then is converted to a compound of formula I (compound 11) as illustrated in the following Reaction Scheme A.

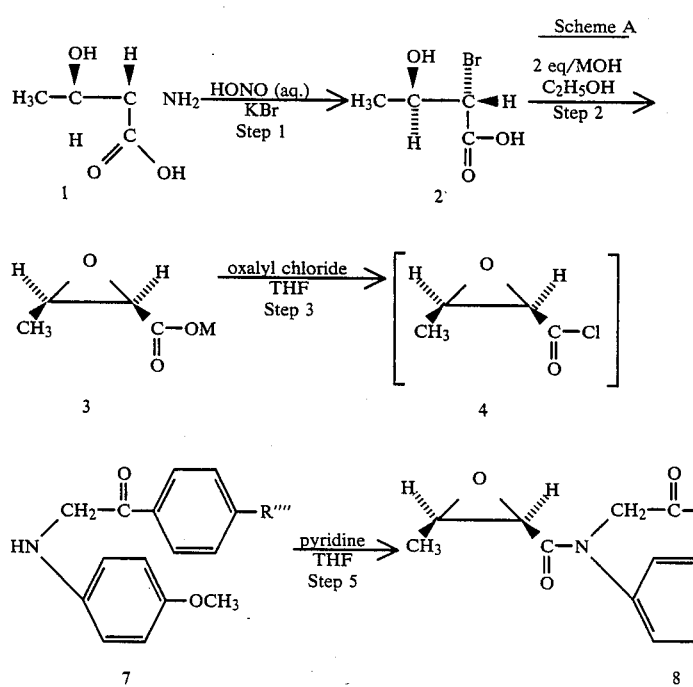

-continued
Scheme A

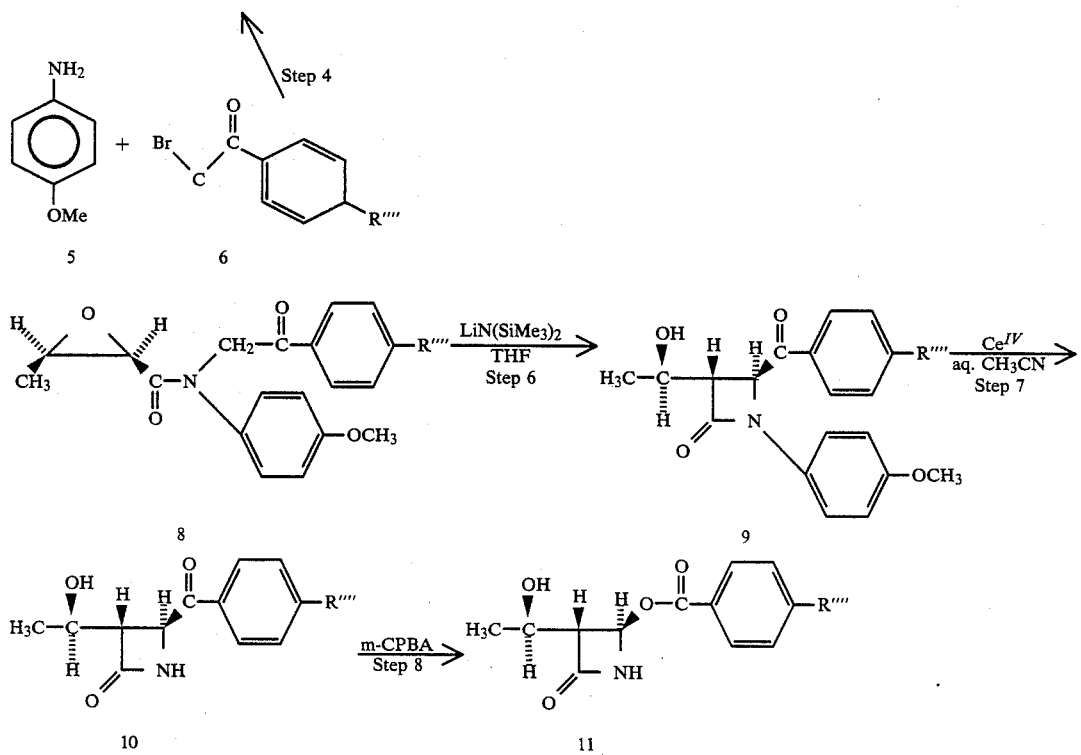

In Step 1 of Reaction Scheme A, (Step A1) L-(−)-threonine is converted to (2S, 3R) 2-bromo-3-hydroxybutyric acid by reaction with an alkali metal bromide, e.g. potassium or sodium bromide and an alkali metal nitrite e.g. potassium or sodium nitrite, in acidic aqueous medium, preferably sulfuric acid, at about 5° C. to 10° C. until the reaction is complete i.e. about 30 minutes.

In Step A2, (2S, 3R) 2-bromo-3-hydroxybutyric acid is converted to potassium (2R,3R)-β-methylglycidate by reaction with an alkali metal base, preferably potassium hydroxide, in a suitable inert solvent, e.g. a lower alkanol, preferably ethanol. If sodium hydroxide is used as the basic reactant, then the sodium salt of the β-methylglycidate is produced. The reaction is carried out at about −5° to 5° C., preferably 0° C.

In Steps A3 and A5 sodium or potassium (2R,3R)-β-methylglycidate is reacted with oxalyl chloride or thionyl chloride under an inert atmosphere, e.g. nitrogen, in an inert organic solvent, e.g. tetrahydrofuran (THF), at a cold temperature, e.g. an ice bath at about 0° C., to form the epoxy acid chloride (compound 4) which is not isolated. The epoxy acid chloride in the inert organic solvent is added to a cool (0° C.) suspension of a phenacyl or substituted phenacyl anisidine hydrochloride (compound 7) in a dry, inert organic solvent, preferably the one in which the epoxy acid chloride is dissolved. The addition is made after an organic base is added to neutralize excess hydrochloride, preferably pyridine or triethylamine. The reaction is continued at room temperature (about 25° C.) until it is completed as evidenced by thin layer chromatography (TLC), yielding (2R,3R)-N-phenacyl-N-(p-methoxy)phenyl-β-methyl glycidamide.

Step A4 illustrates the preparation of a phenacylanisidine-hydrochloride (compound 7) by the reaction of a phenacylbromide (compound 6) and p-anisidine under an inert atmosphere, e.g. nitrogen, in an inert organic solvent, e.g. THF. Subsequently treating with HCl gas precipitates the product as the HCl salt. Other salts of strong organic and inorganic acids can be made by substituting the acid for the HCl gas in the reaction, for example, salts can be formed from the following acids; mineral acids, e.g. HBr, HI; sufuric acid; oxalic acid; trifluoroacetic acid and the like.

In Step A6 (3S,4S,5R)-N-(p-methoxyphenyl)-3-(1-hydroxyethyl)-4-benzoylazetidinone is prepared by reacting the product of Steps A3 and A5 with a strong base, preferably lithium hexamethyldisilazide or potassium carbonate in DMF, in an inert organic solvent, e.g. THF, under an inert atmosphere, e.g. a nitrogen atmosphere, at about −5° C. The reaction is quenched when completed in about 15 minutes with ammonium chloride. Completion of the reaction is evidenced by TLC.

In Step A7 (3S,4S,5R)-3-(1-hydroxyethyl)-4-benzoyl azetidinone is prepared by removal of the para methoxy phenyl group oxidatively from the product of Step A6, e.g. by reaction in aqueous inert organic solvent, e.g. acetonitrile or THF, with aqueous ceric ammonium nitrate, or reaction with ozone in a lower alkanol, a lower alkyl ester of a lower alkanoic acid or acetic acid, until the reaction is complete. Completion of the reaction is evidenced by TLC.

In Step A8, the product of Step A7 is reacted with a per acid, e.g. m-chloroperoxybenzoic acid (m-CPBA), trifluoropeeracetic acid and the like, in an inert organic solvent, e.g. chloroform, for about one day at room temperature to yield (3S,4R,5R)-3-(1-hydroxyethyl)-4-benzoyloxy-azetidinone (compound 11). Completion of the reaction is evidenced by TLC.

In the following Reaction Scheme B, L-(—)-threonine is converted to compound 11 via compounds 12 and 13 to make compound 8 of Reaction Scheme A, then following reaction Scheme A, compounds 9, 10 and 11 are made. Reaction Scheme B is illustrated as follows:

SCHEME B

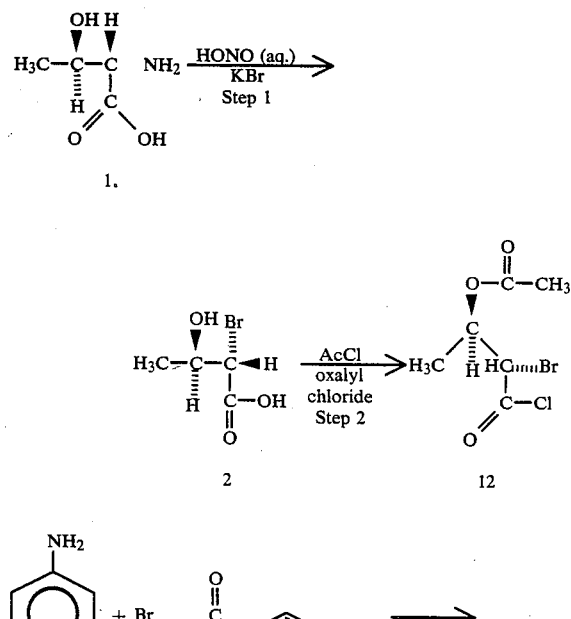

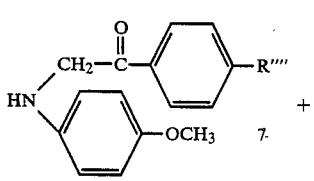

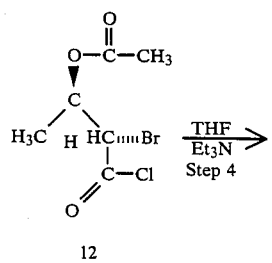

-continued
SCHEME B

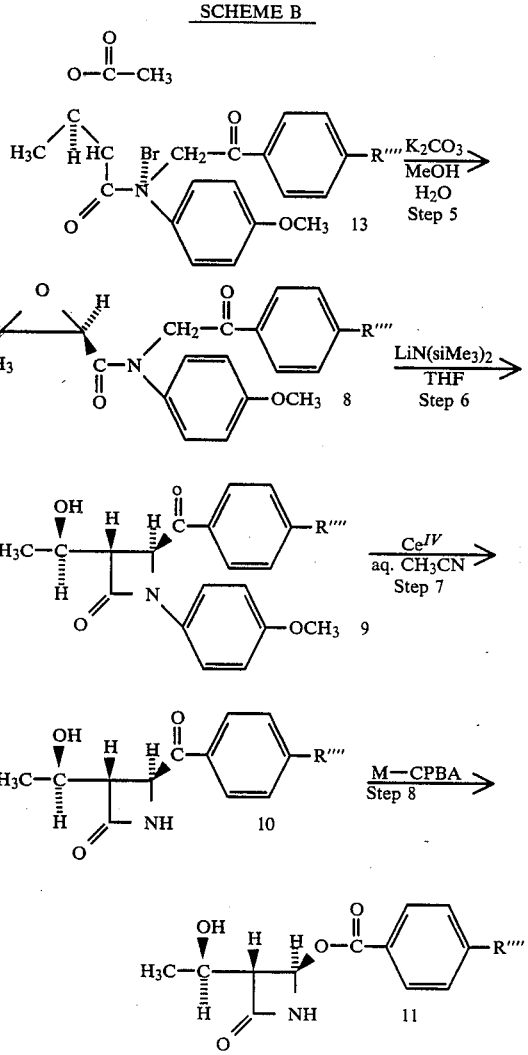

In Reaction Scheme B, Step 1 (Step B1) is identical to Step A1 of Reaction Scheme A and Steps B3, B6, B7 and B8 are identical to Steps A4, A6, A7 and A8 respectively of Reaction Scheme A.

In Step B2, (2S,3R)-2-bromo-3-acetoxybutyryl chloride is prepared by the reaction of (2S,3R)-2-bromo-3-hydroxybutyric acid with acetyl chloride then the reaction mixture is reacted with oxalyl chloride or thionyl chloride in an inert organic solvent, e.g. toluene, at about 0° to 10° C. under an inert atmosphere, e.g. nitrogen, until the reaction is complete in about 30 minutes.

In Step B4, (2S,3R)-2-bromo-3-acetoxybutyryl chloride is reacted with a phenacylanisidine hydrochloride (compound 7) in a dry, inert organic solvent, e.g. THF. The excess hydrochloride is then taken up by a base, e.g. triethylamine or pyridine, under an inert atmosphere, e.g. nitrogen. The resulting product, (2S,3R)-[N-(p-methoxyphenyl)-N-phenacyl]-2-bromo-3-acetoxybutyramide, is recovered.

In Step B5, the compound produced in Step B4, dissolved in a water-miscible inert organic solvent, e.g. methanol, is reacted with aqueous alcoholic potassium carbonate for about thirty minutes to yield (2R,3R)-N-phenacyl-N-(p-methoxy)-phenyl-β-methylglycidamide.

Steps B6, B7 and B8 are identical to Steps A6, A7 and A8 respectively.

Although Reaction Scheme A is the preferred process, Scheme B has certain reactions common therewith. Thus, both Scheme A and Scheme B provide a means to produce the intermediate compounds 8, 9 and 10 starting with L-threonine. The key intermediate in Schemes A and B is compound 8 and the key steps in the process are the conversion of compound 8 to compound 11 via compounds 9 and 10.

Thus, a preferred aspect of this invention comprises a process of producing a compound represented by the formula

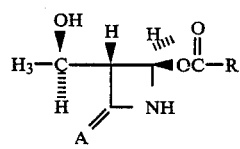

wherein R is phenyl or substituted phenyl wherein the substituents are lower alkyl or halogen; which comprises (a) reacting a compound represented by the formula

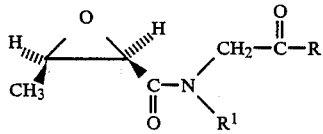

wherein R is as defined for formula Ia and R' is allyl or mono or dimethoxy-phenyl with lithium hexamethyldisilazide;

(b) reacting the product of step (a) with aqueous ceric ammonium nitrate and (c) reacting the product of step (b) with m-chloroperoxybenzoic acid to yield compound I(a).

In a third process aspect of this invention, illustrated by Reaction Scheme C, compound 3, prepared as shown in Reaction Scheme A, Steps A1 and A2, is ultimately converted to compound 10 which is an intermediate common to Reaction Schemes A and B and is used to prepare compound 11 in the same manner as in Reaction Schemes A and b. The following illustrates Reaction Scheme C

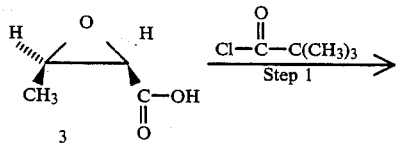

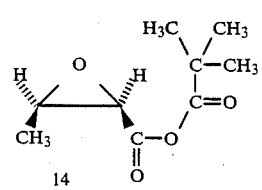

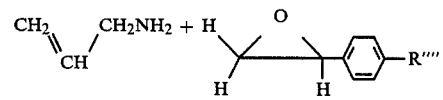

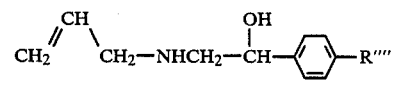

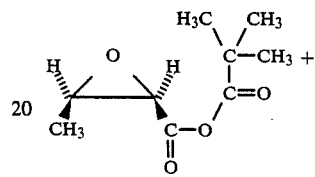

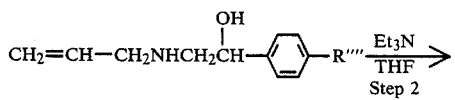

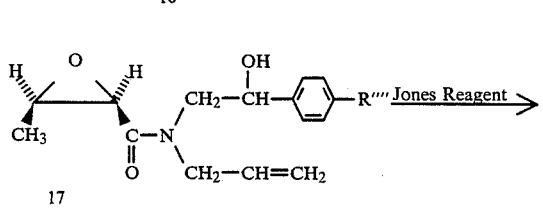

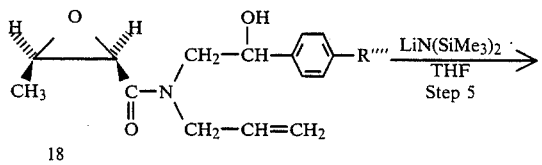

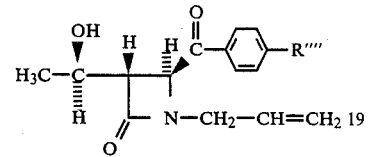

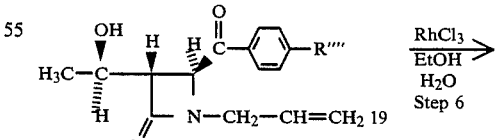

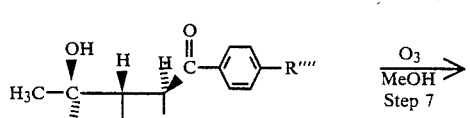

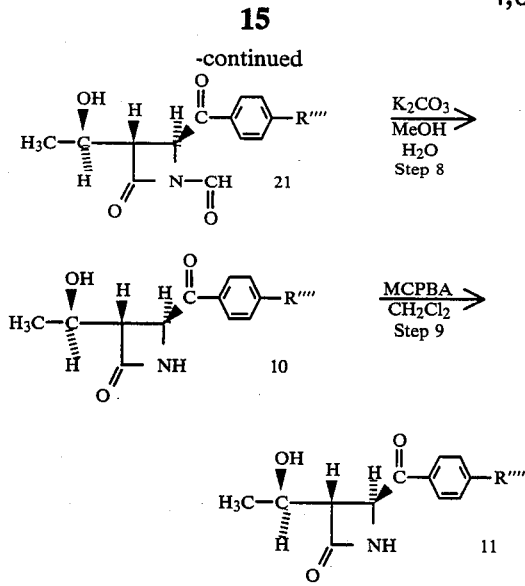

In Step C1, potassium (2R,3R)-β-methyl glycidate, prepared as in Scheme A, Step A2, in suspension in an anhydrous, inert organic solvent, e.g. THF, at about 5° C., is reacted with a sterically hindered acid chloride, preferably pivaloyl chloride, to produce compound 14. Compound 14 is not isolated but is used in the next reaction step in situ.

In Step C2, N-allyl-2-amino-1-phenylethanol, in an inert organic solvent, e.g. THF, is reacted with compound 14 in the presence of an organic base, e.g. triethylamine or pyridine, until completed, as evidenced by TLC, for, e.g. about 90 minutes, to obtain (2R,3R)-[N-(2-phenylethan-2-ol)-N-allyl]-β-methylglycidamide (Compound 17).

In Step C3, N-allyl-2-amino-1-phenylethanol used in step C2 is prepared by reacting styrene oxide and allylamine at reflux under an inert atmosphere, e.g. nitrogen, for about one day.

In Step C4, the product of Step C2, which does not have to be purified, dissolved in acetone is reacted with Jones Reagent, i.e. chromic anhydride in dilute sulfuric acid, at about 15° C. to 20° C. until the reaction is completed as evidenced by TLC for, e.g. about 40 minutes, to produce (2R,3R)-(N-phenacyl-N-allyl)-β-methylglycidamide.

In Step C5, the compound from Step C4, at about −20° C. in an inert, organic solvent, e.g. THF, is reacted with a strong base, preferably lithium hexamethyldisilazide in the same solvent or potassium carbonate in DMF to produce (3S,4S,5R)-N-allyl-3-(1-hydroxyethyl)-4-benzoylazetidinone.

In Step C6, the compound from Step C5 is isomerized to (3S,4S,5R)-N-(1-propenyl)-3-(1-hydroxyethyl)-4-benzoylazetidinone by refluxing with a transition metal catalyst, e.g. RhCl₃, (CH₃CN)₂PdCl₂, (Ph₃P)₃RhCl preferably rhodium chloride, under an inert atmosphere, e.g. nitrogen, in aqueous lower alkanol, e.g. ethanol, for about 45 minutes until the reaction is completed as evidenced by TLC.

In Step C7, the vinyl group of the compound of Step C6 is ozonized in methanol at −70° C. by bubbling in ozone in oxygen until the reaction mixture turns pale blue. The mixture is then purged with nitrogen to yield (3S,4S,5R)-N-formyl-3-(1-hydroxyethyl)-4-benzoylazetidinone. It is also possible and preferred to remove the vinyl group with KMnO₄ to produce compound 10.

In Step C8, if used, the compound from Step C7, compound 21, is converted to (3S,4S,5R)-3-(1-hydroxyethyl)-4-benzoylazetidinone (compound 10) by reaction with aqueous potassium carbonate in methanol at room temperature until the reaction is completed, for about 15 minutes, as evidenced by TLC.

In Step C9, the compound of Step C8 is converted to (3S,4R,5R)-3-(1-hydroxyethyl)-4-benzoyloxyazetidinone as in Reaction Scheme A, Step A8.

The following Examples illustrate the invention:

EXAMPLE 1

(2S,3R)-2-Bromo-3-Hydroxybutyric Acid

To 500 mL of distilled water, cooled at 5°–10° C., was added 30 mL of concentrated H₂SO₄ with stirring over 20 minutes. Then 25 gms L-(−)-threonine and 100 gms of sodium bromide were added. Finally, a solution of 22 gms of sodium nitrite in 65 mL of water was added via a pressure equalized addition funnel over 0.5 hrs. The reaction mixture was removed from the ice bath and stirred an additional 0.5 hrs. Then 10 gms of sodium bisulfite was added in small portions and stirred for an additional 1.5 hrs. The reaction mixture was extracted with ether (2×600 mL), dried (MgSO₄) and solvent was evaporated at reduced pressure. The residue was kept under high vacuum for 20 hrs. to yield the title compound. H¹ NMR (CDCl₃): δ 7.5 (br, 5), 4.0–4.5 (m, 2H), 1.30 (d, 3H, J=6 H$_z$).

EXAMPLE 2

Potassium (2R,3R)-β-Methylglycidate

To a solution of 2 (1.65 gm) in 20 mL of anhydrous ethanol at 0° C., was added a solution of 1.25 gms of KOH in 25 mL of ethanol with stirring. The reaction mixture was stirred at room temperature for 0.5 hrs. and then solvent was evaporated under vacuum with warming. Dry THF was evaporated from the solid residue several times to remove traces of ethanol and then the powdered solid was placed under high vacuum overnight to yield the title compound. It is not necessary to remove potassium bromide by-product for subsequent step. H¹ NMR (D₂O): δ 3.1–3.6 (m, 2H), δ 1.25 (d, 3H, J=6 Hz).

EXAMPLE 3

Phenacyl Anisidine Hydrochloride

To a solution of phenacyl bromide (10 gms) in THF (200 mL), was added p-anisidine (13.6 gms). The mixture was refluxed under nitrogen for 2¼ hrs. The mixture was cooled to 10° C. to precipitate excess p-anisidine hydrobromide. The precipitate was removed by filtration. The filtrate was washed with brine (1×100 mL), dried (MgSO₄), filtered and then a solution of HCl (g) dissolved in dry THF was slowly added until no further precipitation of product occurred. Phenacyl anisidine hydrochloride was collected by filtration and recrystallized from ethanol.

EXAMPLE 4

(2R,3R)-N-Phenacyl-N-(p-Methoxy)Phenyl-β-Methyl Glycidamide

The crude β-methyl glycidic acid potassium salt (2.8 gms) and 5 drops of pyridine was suspended in 30 mL of dry THF and cooled in an ice bath under a Nitrogen atmosphere. One equivalent of oxalyl chloride (1.49 gms) in 2 mL of THF was slowly added via syringe to the stirred suspension and bubbling commenced immediately. Stirring was continued for one hour under a nitrogen atmosphere. In a separate flask, phenacyl anisidine hydrochloride was suspended in dry THF (30 mL) and cooled to 0° C. Pyridine (3 mL) was added followed immediately by the THF solution of the epoxy acid chloride. The mixture was removed from the ice bath and stirred at room temperature under nitrogen for one hour. Brine was added (50 mL). The organic layer was washed with aqueous tartaric acid, followed by aqueous 5% sodium bicarbonate, dried (MgSO$_4$) and concentrated to an oil under reduced pressure. Chromatography on silica gel (10% EtOAc/CH$_2$Cl$_2$) afforded the title compound.

Ms, m+/z=325, H$^1$ NMR (CDCl$_3$): δ 7.8 (m, 2H), 7.6–7.0 (m, 5H), 6.8 (d, 2H, J=9.5 Hz), 5.32 (d, 1H, J=17.5 Hz), 4.8 (d, 1H, J=17.5 Hz), 3.75 (s, 3H), 3.3 (d, 1H, J=4.8 Hz), 3.0 (pentet, 1H, J=5 Hz), 1.4 (d, 3H, J=5 Hz).

EXAMPLE 5

(3S,4S,5R)-N-(p-Methoxyphenyl)-3-(1-Hydroxyethyl)-4-Benzoylazetidinone

The epoxyamide (0.233 gms) produced in Example 4 was dissolved in 3 mL of dry THF and cooled to −5° C. under a nitrogen atmosphere. Then 0.75 mL of 1M lithium hexamethyldisilazide in THF was added via syringe and stirred for 15 minutes at −5° C. To quench the reaction, 10 mL of sat. ammonium chloride (aq.) was added and the product was extracted into EtOAc (2×15 mL). The organic layer was washed with water (10 mL), dried (MgSO$_4$) and solvent was evaporated under vacuum. The resulting title compound was purified by preparative TLC (15% EtOAc/CH$_2$Cl$_2$).

H$^1$ NMR (CDCl$_3$): δ 8.18 (m, 2H), 7.3–7.8 (m, 3H), 7.16 (d, 2H, J=8.8 Hz), 6.75 (d, 2H, J=8.8 Hz), 5.50 (d, 1H, J=2.0 Hz), 4.28 (pent., 1H, J=6.0 Hz), 3.18 (dd, 1H, J=2.0, 6.0 Hz), 3.18 (dd, 1H, J=2.0, 6.0 Hz), 1.27 (d, 3H, J=6.0 Hz).

EXAMPLE 6

(3S,4S,5R)-3-(1-Hydroxyethyl)-4-Benzoyl-Azetidinone

The azetidinone (154.2 mgs) produced in Example 5 was dissolved in H$_2$O/THF (1:6) and to this solution was added ceric ammonium nitrate (682 mgs) in 2 mL of H$_2$O. The reaction was allowed to proceed for 15 minutes and then 10 mL of sat. aq. ammonium chloride was added and product was extracted into EtOAc (2×20 mL). The organic phase was washed with 10% Na$_2$SO$_3$ (aq.) (25 mL) and then brine (10 mL), dried, (MgSO$_4$) and solvent was evaporated under vacuum. Prep. tlc on silica gel (20%) EtOAc/CH$_2$Cl$_2$) to yield the title compound. H$^1$ NMR (CDCl$_3$): δ 8.1 (d, 2H, J=7.5 Hz), 7.3–7.65 (m, 3H), 6.65 (br.s, 1H), 5.07 (d, 1H, J=2 Hz), 4.25 (m, 1H), 3.20 (m, 1H), 1.31 (d, 3H, J=6 Hz).

EXAMPLE 7

(3S,4R,5R)-3-(1-Hydroxyethyl)-4-Benzoyloxy-Azetidinone

The 4-ketoazetidinone, (67.3 mgs) produced in Example 6 was dissolved in 5 mL of chloroform and a solution of m-chloroperoxy benzoic acid (285 mgs) in 5 mL of chloroform was added.

The mixture was kept at 25° C. overnight (20–24 hrs). The mixture was then treated with a solution of 10% Na$_2$SO$_3$ (aq.) and then the organic layer was washed with 10% NaHCO$_3$ (aq.), dried (MgSO$_4$) and solvent was evaporated under vacuum. Purification by prep. tlc (20% EtoAc/CH$_2$Cl$_2$) to yield the title compound. H$^1$ NMR (CDCl$_3$): δ 7.95 (m, 2H), 7.25–7.7 (m, 3H), 6.7 (br.s, 1H), 6.0 (s, 1H), 4.25 (pent., 1H, J=5.5 Hz), 3.3 (d, 1H, J=5.5 Hz), 1.4 (d, 3H, J=5.5 Hz).

EXAMPLE 8

(2S,3R)-2-Bromo-3-Acetoxybutyrychloride

The bromohydrin acid (3.6 gms) produced in Example 1 was placed in a 25 mL round bottom flask and acetyl chloride (2.0 mL) was added with stirring and cooling. After a few minutes the reaction was removed the ice bath and kept at room temperature under nitrogen fro 30 minutes. The mixture was then heated to 40°–45° C. for 30 minutes, cooled to 10° C. and oxalyl chloride (2.5 mL) and toluene (1 mL) was added. The mixture was removed from the ice bath and kept at room temperature under nitrogen for 30 minutes. The reaction mixture was then heated to 50° C. for 30 minutes. Excess toluene and acetyl chloride were removed by fractional distillation (N$_2$, atmospheric). Product was distilled at 10 mm vacuum at 60°–65° C. to give purified title compound. H$^1$ NMR (CDCl$_3$): δ 5.35 (pent., 1H J=6 Hz), 4.65 (d, 1H, J=5 Hz), 2.05 (s, 3H), 1.40 (d, 3H, J=6 Hz).

EXAMPLE 9

(2S,3R)-[N-(p-Methoxyphenyl)-N-Phenacyl]-2-Bromo-3-Acetoxybutyramide

Phenacylanisidine hydrochloride (200 mgs) and the bromoacetoxybutyrylchloride (1.53 mgs) produced in Example 8, were suspended in 2 mL of dry THF and cooled to 10° C. A solution of triethylamine (150 mgs) in THF (1 mL) was slowly added. The mixture was warmed to room temperature and kept under a nitrogen atmosphere for 2 hours. The reaction mixture was then partitioned between water (15 mL) and EtOAc (15 mL). The organic phase was washed with 5% tartaric acid (aq.) and then brine (10 mL each). The organic layer was dried (MgSO$_4$) and product was purified by preparative tlc (5% acetone/CH$_2$Cl$_2$) to yield the title compound. H$^1$ NMR (CDCl$_3$): δ 7.83 (m, 2H), 7.25–7.6 (m, 5H), 6.85 (d, 2H, J=9 Hz), 5.4 (d, 1H, J16 Hz), 5.1–5.5 (m, 1H), 4.65 (d, 1H), J=16 Hz), 4.24 (d, 1H, J=9 Hz), 3.75 (s, 3H), 2.0 (s, 3H), 1.35 (d, 3H, J=6 Hz).

EXAMPLE 10

(2R,3R)-N-Phenacyl-N-(p-Methoxy)Phenyl-β-Methyl Glycidamide

The α-bromo-β-acetoxyamide (230 mgs) produced in Example 9 was dissolved in 3 mL of methanol. A solution of 200 mgs. of potassium carbonate in 1 mL water was added. Additional methanol was added until cloudiness disappeared. The reaction was complete after 30 minutes. A dilute solution of ammonium chloride was added (5 mL) and product was extracted into EtOAc. The organic layer was dried (MgSO$_4$) and solvent was evaporated under vacuum. Product was identical in all respects to that produced in Example 4.

EXAMPLE 11

N-Allyl-2-Amino-1-Phenylethanol

A mixture of styrene oxide (24 mL, 0.2 moles) and allylamine (60.8 mL, 0.8 moles) was heated to reflux under nitrogen atmosphere, for 24 hours. Upon cooling, product crystallized and was triturated with hexane. Recrystallization from hexane afforded the title compound essentially uncontaminated by the other possible regioisomer. Ms m+/z=177; H$^1$ NMR (CDCl$_3$): δ 7.3 (br.s, 5H), 5.6–6.1 (m, 1H), 4.9–5.4 (m, 2H), 4.75 (m, 1H), 3.2 (br.d, 2H), 2.9 (br.s, 2H), 2.7 (m, 2H).

EXAMPLE 12

(2R,3R)-[N-(2-hydroxy-2-phenylethyl-N-Allyl]-β-Methylglycidamide

The bromohydrin acid (1.04 gms) produced in Example 1 was converted to potassium-(2R,3R)-β-methylglycidate as previously described in Example 2. The solid residue was suspended in anhydrous THF and cooled to 5° C. before adding 0.77 mL of pivaloylchloride via syringe. The mixture was removed from the cold bath and stirred vigorously under nitrogen for 30 minutes. Then, 1.00 gms of the amine from Example 11, dissolved in 5 mL of the THF, was added, followed by 0.87 mL of triethylamine in 5 mL of THF. The reaction was removed from the cold bath and the reaction was allowed to proceed for 1.5 hours. The mixture was diluted with water (25 mL) and product was extracted into ether (2×30 mL). The organic layer was washed with 5% tartaric acid (aq.) and brine (1×20 mL each), dried (MgSO$_4$) and concentrated to an oil under vacuum. Product was purified by silica gel chromatography (30% EtOAc/CH$_2$Cl$_2$) to yield the title compound. ms, m+/z=261, H$^1$ NMR (CDCl$_3$): δ 7.25 (s, 5H), 5.3–5.9 (m, 1H), 4.8–5.3 (m, 2H), 2.9–4.4 (m, 7H), 1.2 (d, 3H, J=6 Hz).

EXAMPLE 13

(2R,3R)-(N-Phenacyl-N-Allyl)-β-Methylglycidamide

The crude alcohol (1.46 gms) from the above procedure, was dissolved in 25 mL of acetone and treated with 3.5 mL of Jones reagent (96.3 gms CrO$_3$ 6 mL conc. H$_2$SO$_4$/50 mL H$_2$O) at 15°–20° C.

After 40 minutes, 30 mL of aq. sodium bicarbonate was slowly added to the reaction mixture and product was extracted into EtOAc (2×25 mL). The organic phase was washed with brine, dried (MgSO$_4$) and solvent was evaporated under vacuum. Chromatography on silica gel (20% EtoAc/CH$_2$Cl$_2$) afforded pure title compound as an oil. ms, m+/z=259, H$^1$ NMR (CDCl$_3$): δ 8.0 (d, 2H, J=7.5 Hz), 7.3–7.7 (m, 3H), 5.5–6.0 (m, 1H), 5.0–5.4 (m, 2H), 5.0–5.4 (m, 2H), 5.0 (d, H, J=18.5 Hz), 4.57 (d, 1H, J=18.5 Hz), 4.15 (dd, 2H, J=18.5, 6 Hz), 3.7 (d, 1H, J=5 Hz), 3.1–3.6 (m, 1H), 1.30 (d, 3H, J=6 Hz).

EXAMPLE 14

(3S,4S,5R)-N-Allyl-3-(1-Hydroxyethyl)-4-Benzoylazetidinone

The purified epoxyamide (8.72 gms) produced in Example 13 was dissolved in 125 mL of anhydrous THF, and cooled to −20° C. A 1M solution of lithium hexamethyl disilazide in THF (43.6 mL) was added via syringe. The mixture was allowed to stir under nitrogen for 1.5 hours. Then 50 L of 5% tartaric acid (aq.) was added and the product was extracted into Et$_2$O (2×75 mL). The organic phase was washed with water (2×25 mL), dried (MgSO$_4$) and solvent was evaporated under vacuum. Trituration with hexane/ether gave pure title compound. (mp: 84°–86° C.): H$^1$ NMR CDCl$_3$: 8.15 (dd, 2H, J=10, 2 Hz), 7.3–7.78 (m, 3H), 5.5–6.1 (m, 1H), 5.1–5.5 (m, 2H), 5.18 (d, 1H, J=2.5 Hz), 4.26 (m, 1H), 4.25 (ddd, 1H, J=19, 6, 2 Hz), 3.75 (dd, 1H, J=19, 7 Hz), 3.15 (dd, 1H, J=8, 2 Hz), 2.0 (br.d, 1H, J=7 Hz), 1.3 (d, 3H, J=7 Hz).

EXAMPLE 15

(3S,4S,5R)-N-Vinylmethyl-3-(1-Hydroxyethyl)-4-Benzoylazetidinone

The N-allyl azetidinone from Example 14 (38.2 mgs) was dissolved in 2.5 mL of EtOH/H$_2$O (20:1) and then RhCl$_3$.3H$_2$O (~0.5 mgs) was added with stirring. The mixture was heated to reflux under N$_2$ atmosphere for 45 minutes. Solvent was evaporated under vacuum and product was purified by preparative tlc to yield the title compound as a crystalline product. mp 144°–148° C. H$^1$ NMR (CDCl$_3$): 8.15 (dm, 2H, J=7.5 Hz), 7.4–7.7 (m, 3H), 6.45 (d, 1H, J=15 Hz), 5.3 (d, 1H, J=2 Hz), 4.90 (sextet, 1H, J=6.5 Hz) 4.27 (m, 1H), 3.12 (dd, 1H, J=6, 2 Hz), 2.6 (br d, 1H, J=4 Hz), 1.6 (d, 3H, 6.5 Hz), 1.25 (d, 3H, J=6 Hz).

EXAMPLE 16

(3S,4S,5R)-N-Formyl-3-(1-Hydroxyethyl)-4-Benzoylazetidinone

The azetidinone (64.1 mgs) produced in Example 15 was dissolved in methanol (4 mL) and cooled to −70° C. Ozone in a stream of oxygen was bubbled into the reaction mixture until a pale blue color appeared. Nitrogen was bubbled through the solution for several minutes prior to addition of dimethyl sulfide (0.5 mL) and allowed to warm to room temperature. The reaction mixture was then diluted with 10% NH$_4$Cl (5 m) and extracted with Et$_2$O (2×20 mL), dried (MgSO$_4$) and concentrated to a glass to yield the title compound. H$^1$ NMR (CDCl$_3$) δ 8.9 (s, 1H), 8.2 (dm, 2H, J=7.5 Hz), 7.4–7.75 (m, 3H), 5.6 (d, 1H, J=2 Hz), 4.3 (m, 1H), 3.22 (dd, 1H, J=6, 3 Hz), 2.5 (br.s), 1.25 (d, 3H, j=6 Hz).

EXAMPLE 17

(3S,4S,5R)-3-(1-Hydroxyethyl)-4-Benzoyl-Azetidinone

The N-formyl azetidinone 2N (40 mgs) produced in Example 16 was dissolved in methanol (1 mL) and a solution of potassium carbonate (30 mgs) in 0.3 mL H$_2$O was added. After 15 minutes at room temperature, the reaction was complete. The mixture was diluted with 5 mL of 10% ammonium chloride (aq.) and product was extracted into EtOAc, dried (MgSO$_4$) and solvent was evaporated under vacuum to yield the title compound which was identical in all respects to the product obtained in Example 6.

EXAMPLE 18

(3S,4S,5R)-3-(1-Hydroxyethyl)-4-Benzoyl-Azetidinone

To a solution of the compound produced in Example 15 (2.6 gms) in acetone (30 mL) at 0° C., was added 15 mL of 1M KMnO$_4$ (aq.). The reaction was stirred for 30 minutes at 20° C. and then diluted with water (20 mL). Product was extracted into ethyl acetate (2×20 mL). The organic layer was washed with brine (2×20 mL), dried (MgSO$_4$) and solvent was removed by distillation at reduced pressure. Product was purified by chromatography on silica gel (20% EtOAc/CH$_2$Cl$_2$) to give pure title product which was identical in all respects to that obtained in Example 6.

The above examples are illustrative only. Compounds with the substituents R, R', R", R'" and R"" as defined above are prepared by substituting the appropriately substituted starting materials in the preceding examples.

We claim:

1. A process for preparing a compound represented by the formula

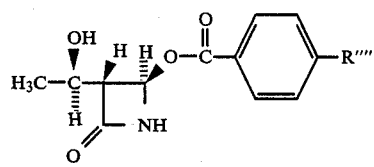

wherein R'''' is hydrogen, halogen or lower alkyl; comprising the steps (a) reacting L-(−)-threonine with an alkali metal bromide and an alkali metal nitrite to produce a compound represented by the formula

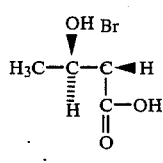

(b) reacting the compound produced in step (a) with an alkali metal base, to produce a compound represented by the formula

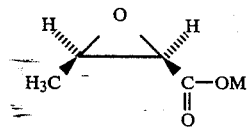

wherein M is an alkali metal (c) reacting the compound produced in step (b) with oxalyl chloride to produce the compound represented by the formula

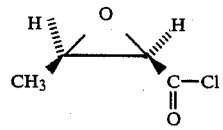

(d) reacting, without isolating, the compound produced in step (c) with a compound represented by the formula

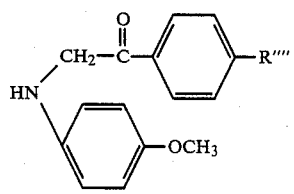

in the presence of an organic base to produce a compound represented by the formula

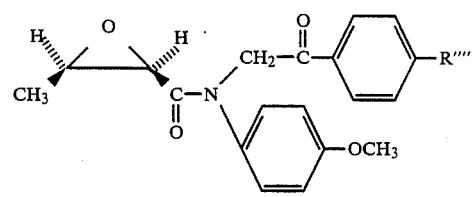

(e) reacting the compound produced in step (d) with a strong base to produce a compound represented by the formula

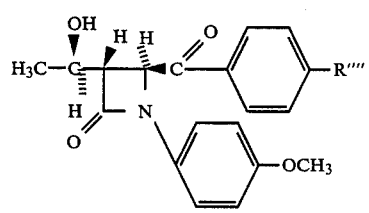

(f) reacting the compound produced in step (e) with aqueous ceric ammonium nitrate or ozone in a lower alkanol, lower alkyl ester of a lower alkanoic acid, or acetic acid to produce a compound represented by the formula

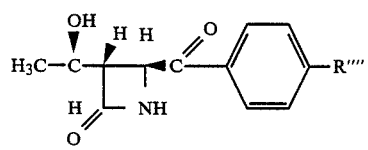

(g) reacting the compound produced in step (f) with a peracid to produce a compound represented by the formula

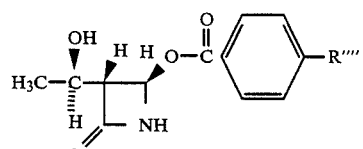

wherein R'''' is as defined hereinabove.

2. The process for claim 1 wherein step (a) the alkali metal bromide is sodium bromide and the alkali metal nitrite is sodium nitrite.

3. The process of claim 1 wherein the step (b) the alkali metal base is potassium hydroxide and M is potassium.

4. The process of claim 1 wherein in step (d) the organic base is pyridine or triethylamine.

5. The process of claim 1 wheein the step (e) the strong base is lithium hexamethyldisilazide.

6. The process of claim 1 wherein in step (g) the peracid is m-chloroperoxybenzoic acid.

7. A process for preparing a compound represented by the formula

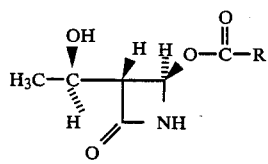

Ia wherein R is phenyl or substituted phenyl wherein the substituents are lower alkyl or halogen; which comprises the steps (a) reacting a compound represented by the formula

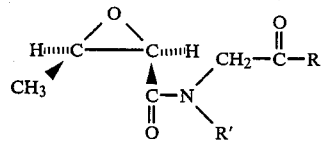

wherein R is as defined for formula Ia and R' is allyl or mono or dimethoxy phenyl with a strong base;

(b) reacting the product of step (a) with aqueous ceric ammonium nitrate or ozone in a lower alkanol, a lower alkyl ester of a lower alkanoic acid or acetic acid; and (c) reacting the product of step (b) with a peracid to yield compound Ia.

8. The process of claim 7 wherein in step (a) the strong base is lithium hexamethyldisilazide.

9. The process of claim 7 wherein in step (c) the peracid is m-chloroperoxybenzoic acid.

* * * * *